United States Patent [19]

Brandt et al.

[11] 4,407,281

[45] Oct. 4, 1983

[54] INTRATRACHEAL TUBE

[76] Inventors: Ludwig Brandt, Heymannstrasse 5, 2000 Hamburg 20; Hellmut Pokar, Strandweg 9, 200 Hamburg 55, both of Fed. Rep. of Germany

[21] Appl. No.: 286,251

[22] Filed: Jul. 23, 1981

[30] Foreign Application Priority Data

Jul. 28, 1980 [DE] Fed. Rep. of Germany ....... 3028568

[51] Int. Cl.³ .................... A61M 15/08; A61M 25/00
[52] U.S. Cl. ................................ 128/207.15; 604/99; 604/100
[58] Field of Search ...................... 128/203.12, 207.15, 128/348, 349 B; 604/88

[56] References Cited

U.S. PATENT DOCUMENTS 3,848,605  11/1974  Harautuneian et al. .
4,324,235   4/1982  Beran ........................... 128/207.15

OTHER PUBLICATIONS

Physical Characteristics of and Rates of Nitrous Oxide Diffusion into Tracheal Tube Cuffs, *Anesthesiology*, vol. 48, No. 6, Jun. 1978.

Primary Examiner—Kyle L. Howell
Assistant Examiner—Karin M. Reichle
Attorney, Agent, or Firm—Hayes, Davis & Soloway

[57] ABSTRACT

An intratracheal tube for giving respiration to a patient, specially during narcosis with a mixture of oxygen and narcotic gas, wherein the intratracheal tube has a respirator hose adapted to be pushed in the windpipe of the patient, the forward end of said hose being surrounded by a blocking sleeve inflatable from the outside with a filling gas and in inflated state abutting closely on the windpipe wall, wherein the inner space of said blocking sleeve is connected in gas-conveying manner, via a connecting hose, to a diffusion vessel situated outside the patient, the surface size, wall thickness and material of said diffusion vessel being chosen so as to make it impervious to the filling gas while permitting the outward diffusion of narcotic gas, specially nitrous oxide gas, in an amount corresponding approximately to the amount diffused into said blocking sleeve.

5 Claims, 6 Drawing Figures

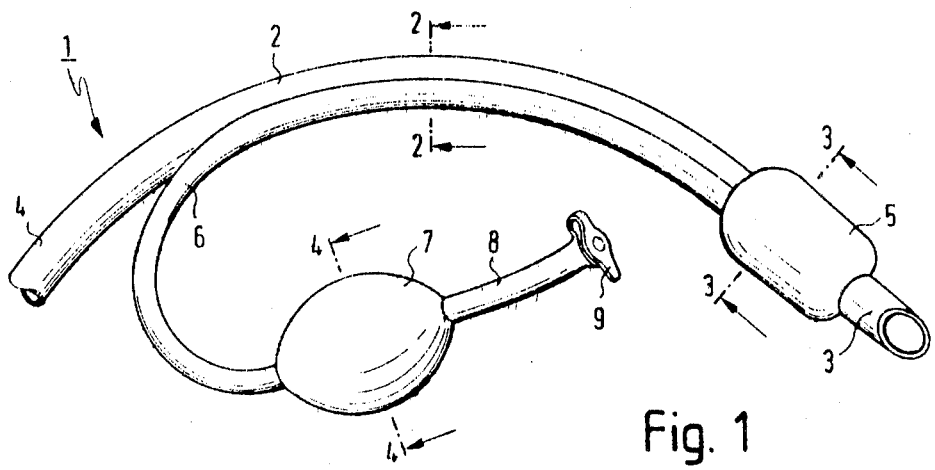
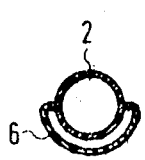
Fig. 2
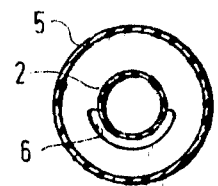
Fig. 3
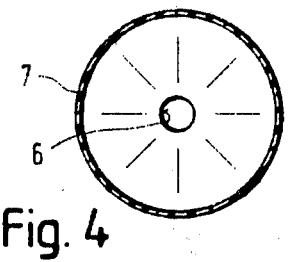
Fig. 4
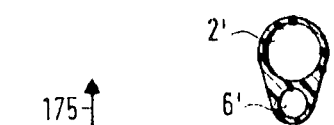
Fig. 5
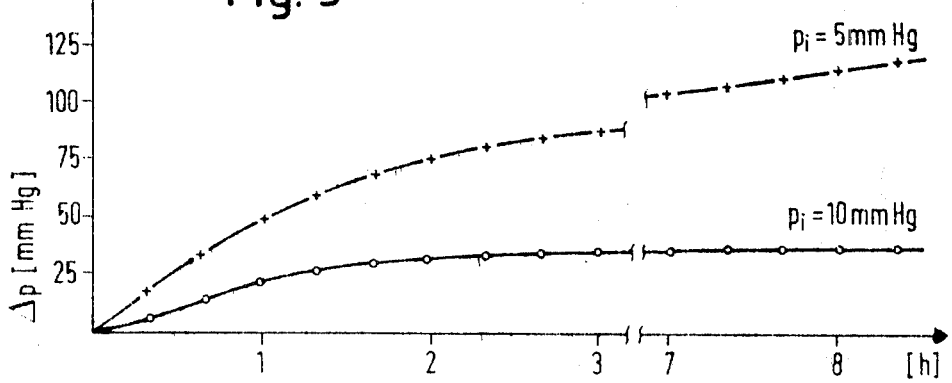
Fig. 6

INTRATRACHEAL TUBE

The invention concerns itself with an intratracheal tube for giving respiration to a patient, specially during a narcosis with a mixture of oxygen and narcotic gas, wherein the intratracheal tube has a respirator hose adapted to be pushed in the windpipe of the patient, the forward end of said hose being surrounded by a blocking sleeve inflatable from the outside with a filling gas and in inflated state abutting closely on the windpipe wall.

Intratracheal tubes are flexible pipes that are pushed into the windpipe through the mouth, through the nose, or through a tracheotomy for imparting narcosis respiration or therapeutic respiration. They consist of tissue-related (compatible) plastics such as gum, silastic or polyvinyl chloride, and they are partly siliconized and thermoplastically deformable. Intratracheal tubes guarantee free respiratory passages. Often, they are equipped with an inflatable blocking sleeve that seals the tracheal lumen around the respiration pipe and thus prevents an aspiration. The blocking sleeve is inflated in situ with atmospheric air via a small duct formed in the pipe wall. The duct changes into a thin hose that is expanded outside of the patient to form a control or pilot balloon. At the end of the hose is an adapter piece for a blocking injector by means of which the blocking sleeve is inflatable.

Sufficient air is introduced to the blocking sleeve to ensure that upon an inspiration no air can escape between the wall of the blocking sleeve and the tracheal wall. The pressure required for this is highly variable. There is a difference between low-presure sleeves having a predetermined sleeve volume that unfolds and high-pressure sleeves, the sealing action of which occurs through inflation with high pressure.

The sealing pressure in low-pressure sleeves amounts to 5–20 mmHg. In high-pressure sleeves the elastic forces of the sleeve material must be overcome, filling pressures of up to 300 mmHg or more being needed for that.

The most frequent complication when intratracheal tubes are used is damage to the mucous membrane of the windpipe in the zone adjacent of the blocking sleeve; see H. Marquort and K.-J. Fischer in the "Periodical Anesthetist", Springer Editing House, vol. 27, 1978, page 187 to 192, in particular page 187, right column. This is caused by the blocking pressure that the sleeve exerts on the tracheal mucous membrane to obtain a good seal. If this pressure exceeds the capillary pressure, there results therefrom a small or zero blood flow in the tracheal mucous membrane in the area of the adjacent sleeve surface. The filling pressure of the low-pressure sleeves corresponds to a large extent to the pressure on the tracheal wall, since the predetermined sleeve volume is chosen so that the necessary filling volume almost always remains below the residual volume, that is, the predetermined sleeve volume; see above loc. cit., pages 188 and following. The filling pressures of the high-pressure sleeves do not completely transmit themselves to the tracheal wall. However, there are no exact measurements. With the above described blocking methods using air, one is most probably operating in pressure ranges that constitute a just tolerable transmural pressure, that is, the portion of the blocking pressure that transmits itself to the tracheal mucous membrane is just tolerable.

Unfortunately in the course of a relatively short inhalation narcosis, the lowest possible blocking pressure obtained using air and the lowest possible transmural pressure do not remain the same, but rise continuously for several hours.

This is because all narcoses are conducted with a certain portion of nitrous oxide gas in the inspiration mixture. This portion can be up to 80%. The rest of the inspiration gaseous mixture is oxygen and under certain circumstances 1–2% of a volatile anesthetic, generally halogenated hydrocarbon. Nitrous oxide gas has the ability to diffuse into the blocking sleeve to an extent depending on time and concentration. Since, conversely, the blocking air cannot diffuse outwardly from the sleeve, there results a volume and pressure rise in the sleeve and therewith a rise of the transmural pressure. Our own measurements in a customary low-pressure sleeve have shown that after initial filling pressures of about 10 mmHg under narcosis conditions with an inspiratory nitrous oxide gas portion of only 66%, the sleeve pressure reached, after one hour, a value of 50–60 mmHg and after a further hour, under narcosis conditions, 100 mmHg. Tests in vitro have shown that a continuous pressure rise in the blocking sleeve can be observed for up to 8 hours, the resulting very high pressure level remaining thereafter. The final pressure depends on the initial blocking pressure and is between 110 and 160 mmHg. In so-called high-pressure sleeves with initial filling pressures of 200 to 300 mmHg, a similar pressure rise by diffusion of nitrous oxide gas is observed. Independently of the kind of blocking sleeve, this overpressure acts in all cases on the mucous membrane of the windpipe.

There have hitherto been proposed the following possibilities for solution of the problem of pressure rise in the blocking sleeve caused by diffusion of nitrous oxide gas:

(1) Recurrent volume reduction of the blocking sleeve in long-lasting narcoses either manually with a plastic injector or with a commercially available instrument specially designed therefor. This method involves a substantial danger of aspiration by allowing too great a reduction of volume or of the re-diffusion of nitrous oxide gas from the sleeve outwardly in the case of an increase in the inspiratory concentration of oxygen that may be needed during the narcosis. In addition, this method is consuming in time and material and is scarcely used in the practice.

(2) Filling the blocking sleeve with the narcotic gaseous mixture. With identical partial pressures no diffusion of nitrous oxide gas takes place. The risk of aspiration also increases here when the inspiration mixture is changed during narcosis or in post-operative subsequent administration of respiration. Although often recommended in the literature, this method is seldom used in the practice.

(3) Intratracheal tube sleeves with excess-pressure valves. Those tubes are offered. But the increased risk already mentioned under (1) above also applies here.

The present invention is based on the problem of improving an intratracheal tube of the kind mentioned above in a manner such that the pressure rise in the blocking sleeve caused by diffusion of nitrous oxide gas is reduced at least to the extent that the transmural pressure is kept at a harmless value. At the same time, the pressure in the blocking sleeve is automatically set so as to make control by the clinic personnel, manual contacts, or expensive valve arrangements for reducing the pressure unnecessary.

The invention solves this problem by an intratracheal tube for giving respiration to a patient, specially during a narcosis with a mixture of oxygen and narcotic gas, wherein the intratracheal tube comprises a respirator hose adapted to be pushed in the windpipe of the patient, the forward end of said hose being surrounded by a blocking sleeve permeable to narcotic gas and inflatable from the outside with a filling gas and in inflated state abutting closely on the windpipe wall, wherein the inner space of said blocking sleeve is connected in gas-conveying manner, via a connecting hose, to an inflation port and to a diffusion vessel situated outside the patient, the surface size, wall thickness and material of said diffusion vessel being chosen so as to make it impervious to the filling gas, but pervious to narcotic gas, thereby permitting the outward diffusion of narcotic gas, specially nitrous oxide gas, in an amount corresponding approximately to the amount diffused into said blocking sleeve.

Therefore, the invention follows a course other than that formerly followed for reducing the pressure rise in the blocking sleeve in case of diffusion of nitrous oxide gase. The invention is based on the following concept:

Since it is not possible to prevent the diffusion of nitrous oxide gas into the blocking sleeve, there must be found a riskless as possible way to lower as uniformly as possible the partial pressure of the nitrous oxide gas in the blocking sleeve. Although there could be provided pressure controlling switches that automatically monitor the partial pressure, the expense for such devices would be too great.

Therefore, it is sought according to the invention to remove by diffusion from the blocking sleeve that portion of nitrous oxide gas which has entered therein by diffusion, that is, by re-diffusion of the nitrous oxide gas to free atmosphere where the partial pressure of said nitrous oxide gas is zero. Accordingly, the blocking sleeve pursuant to the invention is connected via a gas conduit with a diffusion vessel, having a diffusion resistance as low as possible, situated outside the patient. The nitrous oxide gas is in this manner uniformly distributed over the entire volume of the blocking sleeve, gas conduit and diffusion vessel, and can be diffused through the wall of the diffusion vessel into the free atmosphere. The surface size of said diffusion vessel and the wall material thereof are chosen so as to allow a substantial portion of the nitrous oxide gas diffused into the blocking sleeve to leave the system by way of the wall of the diffusion vessel so as to keep within acceptable limits the pressure rise produced in the blocking sleeve by the nitrous oxide gas diffusion thereto and the rise of transmural pressure associated therewith.

According to a preferred embodiment of the invention, a control or pilot balloon generally present in such intratracheal tubes is constructed as a diffusion vessel by choosing the surface and wall material thereof in accordance with the requirements above mentioned. Said pilot balloon as hitherto can be used and constructed for the purpose of making it possible to verify by touch the sleeve filling and approximate filling pressure—of course only with extensive experience.

It is true that also through the wall of hitherto used pilot balloons a certain portion of nitrous oxide gas diffuses outwardly into the room atmosphere; see F. Scheurecker et al in the periodical "Anesthetist", Springer Editing House, 1978, vol. 27, pages 336 to 339, in particular 338, left column and page 339, bottom of left column. In the tests described in these passages of the literature, the pressure rise of the blocking sleeve was measured with and without a pilot balloon, which in the citations was called a balancing balloon. The measurements ran for a maximum of 135 minutes and showed a reduced pressure rise in the blocking sleeve when such a balancing balloon was used. Here the pressure rise in the blocking sleeve was between 10 and 20 mmHg; these values depend on the concentration of nitrous oxide gas and have been essentially confirmed by tests conducted by the applicant. In the long-term tests conducted by the applicant with high-pressure and low-pressure sleeves, it was established that the pressure rise in the blocking sleeve can amount to between 100 and 160 mmHg depending on the initial filling pressure; but this pressure rise represents an already dangerous transmural pressure on the mucous membrane of the windpipe.

From the above mentioned measurements by Scheurecker and others, as in the corresponding tests by the applicant, there is recorded a continuous pressure rise in the blocking sleeve, this pressure rising continuously, and after an initial time almost linearly, over a long measuring period of eight hours, for instance, as demonstrated by the applicant.

The solution proposed by the invention of making use of the diffusion of nitrous oxide gas in the room atmosphere for reducing the pressure in the blocking sleeve by enlarging the re-diffusion surface of the nitrous oxide gas and adquately selecting the material of the diffusion vessel shows surprising further advantages. On the one hand, the pressure rise resulting from the volume enlargement of the system which includes the blocking sleeve, connecting hose and diffusion vessel (or balancing balloon) proceeds more slowly than in the formerly known intratracheal tubes.

In addition, in this system comprising a blocking sleeve, connecting hose and diffusion vessel, there is established after one to two hours, when the connecting hose and the diffusion vessel are adequately dimensioned, a diffusion equilibrium: In this state of equilibrium the amount of the nitrous oxide gas diffused into the blocking sleeve is the same as the amount of nitrous oxide gas diffused outwardly into the room atmosphere so that from this moment the inner pressure of the blocking sleeve and therewith also the transmural pressure exerted by the sleeve on the mucous membrane of the windpipe remain constant. The height of this equilibrium pressure, with a corresponding dimensioning of the diffusion vessel, depends essentially on the dimensions of the connecting hose between blocking sleeve and diffusion vessel. The diffusion resistance of this connecting hose must therefore be as low as possible, that is, the cross-sectional surface thereof must be as large as possible.

It could be demonstrated in tests that in conventional intratracheal tubes with low-pressure blocking sleeves in which only the pilot balloon was exchanged for a corresponding diffusion vessel according to the invention, the inner pressure of the blocking sleeve of initially 12.5 mmHg adjusted itself within about two hours to a final pressure of about 45 mmHg, and it was possible to keep said final pressure constant for another 12 hours.

Substantially better results can be obtained if the connecting hose between blocking sleeve and diffusion vessel is enlarged in cross section so that the nitrous oxide gas diffused into the blocking sleeve can be distributed with poor resistance over the whole system of blocking sleeve, connecting hose and re-diffusion vessel: In this case there is obtained a maximum pressure increase of between 15 and 20 mmHg.

The invention is explained in more detail in the following example with reference to the drawings, wherein:

FIG. 1 is a view of an intratracheal tube comprised of respiration hose and blocking sleeve that is connected by a connecting hose with a balancing balloon;

FIG. 2 is a cross section through the intratracheal tube shown in FIG. 1 along line 2—2;

FIG. 3 is a cross section through the intratracheal tube in FIG. 1 along line 3—3;

FIG. 4 is a cross section through the intratracheal tube in FIG. 1 along line 4—4;

FIG. 5 is a cross section through respirator and connecting hose for a modified intratracheal tube; and FIG. 6 is a diagram traced all along for the pressure rise $\Delta p$ in mmHg within a low-pressure blocking sleeve of an intratracheal tube of known type and of an intratracheal tube according to the invention.

An intratracheal tube 1 includes a respirator hose 2 of a tissue-related plastic material the forward end 3 of which is introduced in the windpipe of a patient and the rear end 4 of which is connected to a respirator or narcosis apparatus, not shown here. The respirator hose 2 is surrounded in the area of the forward end thereof by a blocking sleeve 5, the respirator hose 2 longitudinally traversing the blocking sleeve; see FIG. 3. The blocking sleeve is conventionally sealed against the respirator hose. At the end of the blocking sleeve 5 remote from the forward end 3 of the respirator hose 2 discharges a connecting hose 6 that is likewise made of tissue-related plastic material and surrounds substantially semi-circularly the respirator hose 2 in the area of the introduced length of the respirator hose; see FIG. 2. The respirator hose 2 and the connecting hose 6 form a double pipe. Of course other constructions are also possible.

Outside the patient the connecting hose 6 extends separately from the respirator hose 2 and discharges in a diffusion vessel or balancing balloon 7. On the side of the balancing balloon 7 opposite said discharge point there is attached to the balloon an adapter piece 8 the free end of which is gastight closed with a three-way tap or a yoke closure 9.

To start the artificial respiration of a patient, the respirator hose 2 is pushed by its forward end into the windpipe of the patient. The blocking sleeve 5 is also made of yielding, tissue-related synthetic material and thereby prevents only insignificantly the pushing of the respirator hose. When the respirator hose is brought to the correct position, then a blocking injector not shown here is attached to the adapter piece 8. With said injector the blocking sleeve 5 is inflated with a filling gas, usually air, to an extent such that the outer wall of the blocking sleeve abuts closely on the tracheal mucous membrane of the patient and seals the tracheal lumen against gas and liquid in order to prevent aspiration. The initial filling pressure $p_i$ of such a low-pressure sleeve is approximately from 5 to 20 mmHg above atmospheric pressure. As soon as the blocking sleeve 5 has been inflated, the blocking injector is withdrawn from the adapter piece 8 and the latter is closed. Thus, in the system comprised of blocking sleeve 5, connecting hose 6, balancing balloon 7 and adapter piece 8 there prevails the original or initial pressure $p_i$ already mentioned.

As soon as the blocking sleeve is in firm position, the patient can safely be given respiration via the respirator hose. During a narcosis the patient is fed an inspiration mixture that contains oxygen, up to 80% nitrous oxide gas and under certain circumstances 1 to 2% of a volatile anesthetic, for instance, halogenated hydrocarbon such as halotane or the like.

Some of the nitrous oxide gas fed to the patient with the inspiration mixture diffuses into the inner space of the blocking sleeve through the wall area of the sleeve that is exposed in the windpipe and via the tracheal tissue through the wall areas of the blocking sleeve that abut on the windpipe. The amount of diffusion depends on the material of the blocking sleeve, on the wall thickness thereof and on the partial pressure of nitrous oxide gas that predominates in the blocking sleeve that in this case is initially zero, since the filling gas was initially air. This nitrous oxide gas in the blocking sleeve moves into and through the connecting hose 6 into the balancing balloon 7. To achieve in the system comprised of blocking sleeve, connecting hose 6 and balancing balloon 7 a partial pressure of nitrous oxide gas as uniform as possible, the cross section of the connecting hose 6 must be as large as possible. This can be obtained, for example, by the double pipe of respirator hose and connecting hoses shown in FIG. 2.

The size of the balancing balloon 7 corresponds at least to the size of the blocking sleeve, but it also can easily be larger. The material and thickness of the wall of the balancing balloon 7 are chosen so that the nitrous oxide gas contained in the balancing balloon can diffuse outwardly in the room atmosphere where the partial pressure of the nitrous oxide gas is zero. The material of the balancing balloon 7 is either identical with the material of the blocking sleeve or is a different material better suited to diffusion of nitrous oxide gas from the balancing balloon. The wall thickness of the balancing balloon is kept as small as possible.

The material and wall thickness of the balancing balloon are chosen so that after a certain start-up time a diffusion equilibrium results, that is, the same amount of nitrous oxide gas per unit of time that diffuses into the blocking sleeve 5 diffuses from the balancing balloon 7 outwardly into the room atmosphere. Long-term measurements for the pressure rise within the blocking sleeve caused by the diffusion of nitrous oxide gas in the blocking sleeve were carried out with the described intratracheal tube. One such measurement running for more than eight hours is shown in FIG. 6 by a broken circular line. The initial pressure within the blocking sleeve amounted in this case to 10 mmHg above the atmospheric pressure. As is to be seen from FIG. 6, the inner pressure of the sleeve rises within the first hour to about 20 mmHg, and already after about 2 hours achieves a final value between 30 and 35 mmHg, which is maintained throughout the measurement. This constant final value depends on the size of the balancing balloon and the material and wall thickness thereof, the same as on the cross section of the connecting hose 6. The calibration curve shown was drawn with an intratracheal tube in which the cross section of the connecting hose 6 was relatively small and had a cross section that corresponded to the connecting hose between balancing control balloon and blocking sleeve in conventional low-pressure intratracheal tubes. According to the cross section of the connecting hose there was obtained with the same balancing balloon final values between 20 and 40 mmHg for the final pressure.

In comparison herewith there is shown in FIG. 6 a calibration curve for the pressure rise within a blocking sleeve of a conventional low-pressure intratracheal tube that has no balancing balloon but only a small pilot balloon. The pressure rise within the blocking sleeve amounted here to about 45 mmHg already after one hour, after two hours to about 75 mmHg, and then rose almost continuously with a gradient between 6 and 4 mmHg. The calibration curve is identified in FIG. 6 by a line including crosses. The initial pressure in the blocking sleeve a mounted to 5 mmHg. As it can be seen from the calibration curve, the inner pressure of the blocking sleeve after about eight hours was at a value of approximately 115 mmHg. With other intratracheal tubes of known type there were measured pressure rises of up to 160 mmHg after eight hours.

From the comparison of the two calibration curves it can be seen that with an intratracheal tube according to the invention the pressure rise in the blocking sleeve is substantially lower than in already known low-pressure tracheal tubes. Besides, the inner pressure after a period of operation oscillates to a constant low value. By this low pressure rise said transmural pressure on the tracheal mucous membrane is only insignificantly increased; no side effects such as bleeding obstacles of the tracheal mucous membrane could be found. Thus, an intratracheal tube according to the invention can be used also for several hours in long operations without danger to the patient. With the intratracheal tube according to the invention there is likewise no additional aspiration danger since the initial filling gas free of nitrous oxide gas remains in the system comprised of the blocking sleeve, connecting hose and balancing balloon for the duration of the artificial respiration or narcosis. Besides, in an intratracheal tube according to the invention the inner pressure of the blocking sleeve needs at no time to be influenced from the outside; on the contrary, the pressure rise in the blocking sleeve is automatically limited to a value of about 30 mmHg which is of no danger for the patient.

As a balancing balloon it is possible, for instance, to use directly a blocking sleeve or a balancing balloon of a material identical with that of the blocking sleeve. In any case the surface size, material and wall thickness of the balancing balloon must be selected so that a considerable portion of the nitrous oxide gas diffused into the blocking sleeve can diffuse via the wall of the balancing balloon outwardly into the room atmosphere.

Even though in the example described and illustrated there was used a balancing balloon in substitution for the otherwise usual pilot balloon of an intratracheal tube, it is obviously possible to take a different course and, for instance, to provide a balancing balloon independent of the filling hose and that is then connected by a connecting hose of its own to the blocking sleeve.

Instead of wrapping the connecting hose partly around the respirator tube, as shown in FIG. 2, it is also possible to form the connecting hose in the wall of the respirator hose; see FIG. 5, so that respirator and connecting hose in the connected area form almost a double pipe 2' and 6'.

Polyvinyl chloride or latex have recommended themselves as material for the blocking sleeve and balancing balloon. A logical combination is to make the blocking sleeve of polyvinyl chloride and the balancing balloon of latex, since latex has for nitrous oxide gas more diffusibility than polyvinyl chloride. The wall thickness of blocking sleeve and balancing balloon is 0.1 mm; the diameter of the connecting hose must amount at least to 1 mm. The volume of the balancing balloon depends on the size of the blocking sleeve used and is between 5 and 100 $cm^3$; a volume of about 20 $cm^3$ is enough in many cases.

Although there has been described above an intratracheal tube of the low-pressure type, it is obvious that the invention can also be used in connection with intratracheal tubes of the high-pressure type where the initial filling volume is between 160 and 300 mmHg. In this case also the properties of the balancing balloon are chosen so that a considerable portion of the nitrous oxide gas diffused in the high-pressure sleeve can be diffused outwardly in the room atmosphere via the balancing balloon.

We claim:

1. An intratracheal tube for giving respiration to a patient, specially during a narcosis with a mixture of oxygen and narcotic gas, wherein the intratracheal tube comprises a respirator hose adapted to be pushed in the windpipe of the patient, the forward end of said hose being surrounded by a blocking sleeve permeable to narcotic gas and inflatable from the outside with a filling gas and in inflated state abutting closely on the windpipe wall, wherein the inner space of said blocking sleeve is connected in gas-conveying manner, via a connecting hose, to an inflation port and to a diffusion vessel situated outside the patient, the surface size, wall thickness and material of said diffusion vessel being chosen so as to make it impervious to the filling gas, but pervious to narcotic gas, thereby permitting the outward diffusion of narcotic gas, specially nitrous oxide gas, in an amount corresponding approximately to the amount diffused into said blocking sleeve.

2. An intratracheal tube according to claim 1, wherein the surface size, wall thickness and material of said diffusion vessel and the inner diameter of said connecting hose are chosen so that in the sealed system comprised of blocking sleeve, connecting hose and diffusion vessel there is attained a diffusion equilibrium whereby the inner pressure of said system is kept at an almost constant final value after a start-up time.

3. An intratracheal tube according to claim 1, wherein said connecting hose between said blocking sleeve and said diffusion vessel is attached with said respirator hose at least in the area where said respiration hose of the intratracheal tube extends into and within the windpipe of the patient in use.

4. An intratracheal tube according to claim 3, wherein said connecting hose is incorporated into the wall of said respiration hose.

5. An intratracheal tube according to claim 3, wherein said connecting hose at least partly encompasses said respirator hose.

* * * * *